United States Patent [19]

Bultman et al.

[11] 4,133,862

[45] Jan. 9, 1979

[54] METHOD OF INHIBITING AND/OR ERADICATING MARINE FUNGAL GROWTH WITH OBTUSASTYRENE

[75] Inventors: John D. Bultman, Oxon Hill, Md.; Donald D. Ritchie, New York, N.Y.; Leonard Jurd, Berkeley, Calif.

[73] Assignee: The United States of America as represented by the Secretary of the Navy, Washington, D.C.

[21] Appl. No.: 804,193

[22] Filed: Jun. 6, 1977

[51] Int. Cl.$^2$ ............................................. A61L 13/00
[52] U.S. Cl. .................................... 422/28; 422/6; 424/346; 427/297; 427/440
[58] Field of Search ................ 21/7, 58; 424/346; 427/297, 440

[56] References Cited

U.S. PATENT DOCUMENTS

| | | | |
|---|---|---|---|
| 3,925,558 | 12/1975 | Bultman et al. | 424/331 |
| 3,951,820 | 4/1976 | Jurd et al. | 21/58 X |
| 3,973,040 | 8/1976 | Jurd | 424/346 |
| 4,012,529 | 3/1977 | Bultman et al. | 21/7 X |
| 4,029,818 | 6/1977 | Jurd et al. | 21/7 X |

*Primary Examiner*—Barry S. Richman
*Attorney, Agent, or Firm*—R. S. Sciascia; Philip Schneider; Thomas McDonnell

[57] ABSTRACT

Marine fungal growth is inhibited and/or eradicated in wood by contacting the wood with obtusastyrene whose formula is:

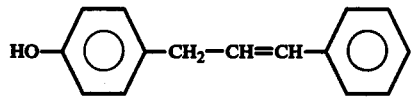

4 Claims, 4 Drawing Figures

METHOD OF INHIBITING AND/OR ERADICATING MARINE FUNGAL GROWTH WITH OBTUSASTYRENE

BACKGROUND OF THE INVENTION

This invention relates generally to methods employing biologically active compounds and more particularly to methods employing fungicides.

Fungal infestation of wood structures in the marine environment is damaging in two ways. Directly, fungi cause, in time, deterioration of the wood structure. But more importantly, evidence indicates that fungal infestation is prerequisite for attack by more destructive organisms such as marine borers. The resulting damage to marine wood structures amounts to hundreds of millions of dollars per year.

Fungicides are divided into two general classes which are referred to as protective and eradicant. The former is applied to prevent fungal infection and serves to kill or inhibit the fungal growth as spores settle on the treated material. Eradicant fungicides are used to destroy or eradicate fungi which have already become established and are actively growing. The major differences in characteristics between the two are that the protective fungicide must, in addition, be extremely stable and persistent.

The presistence and stability requirements for protective fungicides on wood in a marine environment are especially high. The water and its motion act to leach out the fungicide or other wood perservatives. This physical phenomena is particularly acute in the warm waters of tropical and subtropical regions. Besides leaching out, some preservatives percolate down the conducting vessels of vertically oriented timbers. These perservatives then collect at the bottom and exude and leach out of the wood. The best example of a preservative having these problems is creosote, which currently has the greatest use. Often creosoted timbers have to be replaced every four or five years on account of deterioration. An additional problem is the resulting pollution to the surrounding water. For example, creosote may be impregnated into pine in amounts as much as 25 lbs/ft$^3$; since creosote is its own solvent, the amount of biologically active material being introduced into the water would be considerable.

SUMMARY OF THE INVENTION

It is therefore an object of this invention to protect wood from fungal attack.

Another object of this invention is to provide a fungicide with a low toxicity to high orders of animals and plants.

A further object of the invention is to render wood resistant to fungal attack for an exceptionally long period of time.

These and other objects are achieved by treating a material, such as wood, with obtusastyrene.

DETAILED DESCRIPTION OF THE INVENTION

Figure 1:
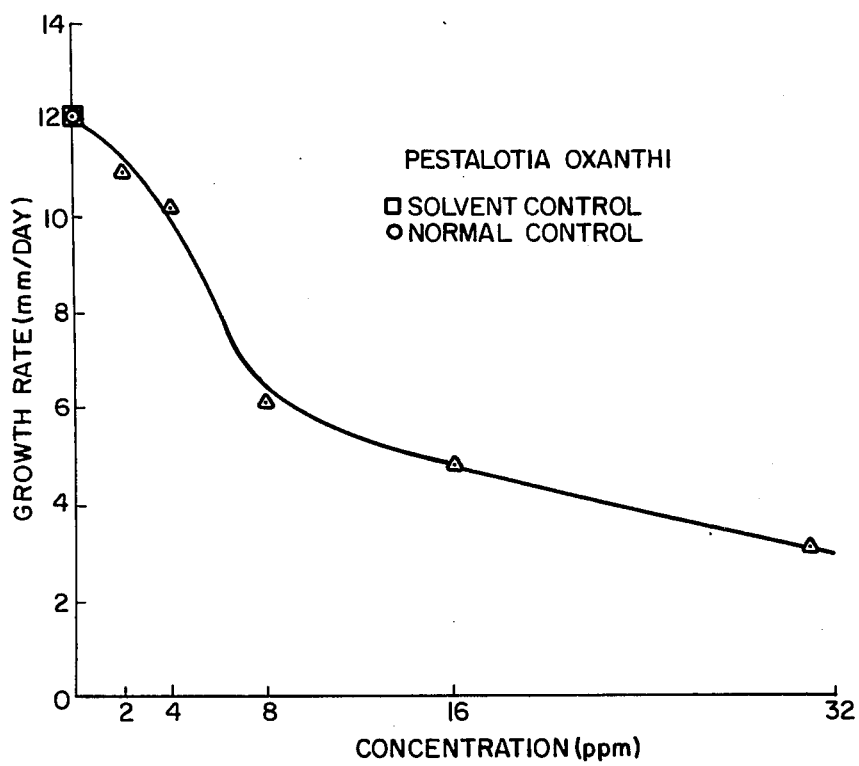
FIG. 1 shows the growth rate of the *Pestalotia oxanthi* colonies as a function of obtusastyrene concentration.
Figure 2:
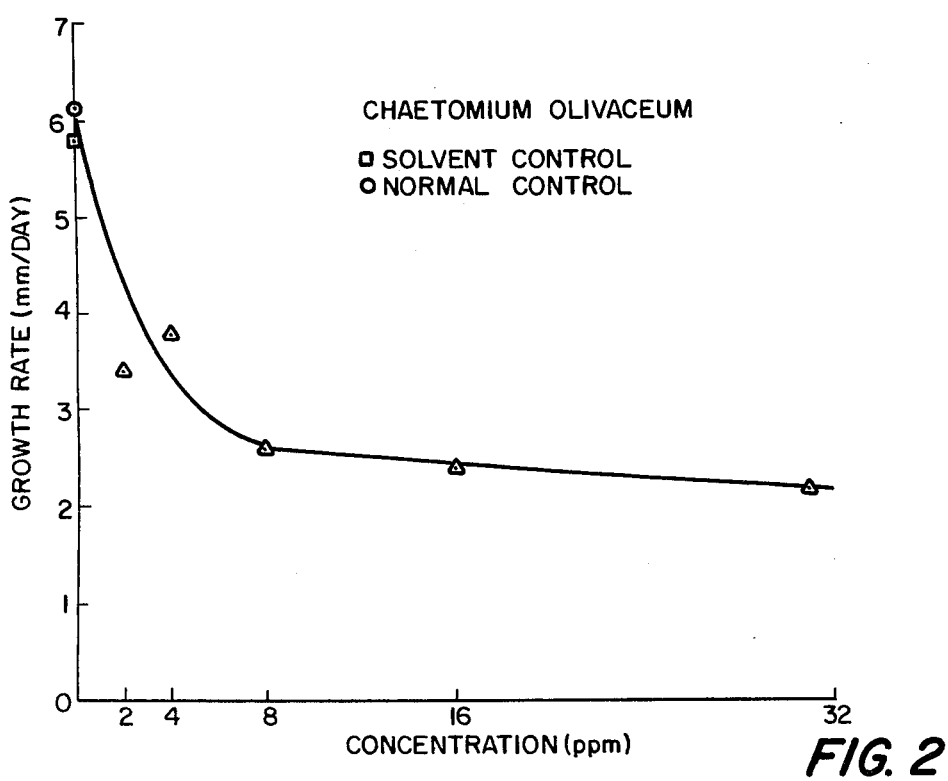
FIG. 2 shows the growth rate of *Chaetomium olivaceum* colonies as a function of obtusastyrene concentration.

The preferred method of impregnating southern yellow pine wood, a widely used wood for marine construction, is a modified Bethel full cell vacuum/pressure technique using conventional wood-treating facilities. This process comprises subjecting a piece of lumber to a vacuum of at least 22 inches of Hg for a predetermined period depending upon the size of the wood to be treated, introducing an obtusastyrene solution into the evacuated working chamber of the impregnating device, subjecting the chamber to about 125–200 psi nitrogen until no more solution is taken up by the wood, releasing the pressure, allowing the panels to remain submerged in the solution for 15 minutes to allow pressure equilibration with the interior of the wood, and applying vacuum and heat to remove excess solvent.

Suitable solvents for obtusastyrene are polar organic solvents such as acetone and ethanol, or nonpolar solvents such as benzene, but the preferred solvent is acetone. The solution concentration for the above process in most cases is about 3 weight percent of obtusastyrene in the selected solvent.

For woods other than the soft southern yellow pine, the pressures and times would be adjusted accordingly. The treatment must be sufficient to impart at least an inch of penetration into the wood. For other applications not requiring a deep penetration of the fungicide, less stringent methods would suffice. Spraying or misting of the fungicide would be used, for example, on wood surfaces or for non-wood applications.

The following experiments are given to demonstrate the inhibitory effects of obtusastyrene on the growth rates and reproduction of two marine fungi. The tests and the results are not intended to limit, in any manner, the scope of the instant invention or the claims to follow.

Organisms used in these tests were the ascomycete *Chaetomium olivaceum* Ames and an imperfect fungus morphologically similar to *Pestalotia oxanthi*, which hereinafter are referred to as Chaetomium and Pestalotia. These are facultative fungi originally isolated from wood panels exposed to a Panamanian estuary. Cultures were maintained on a glucose-yeast extract medium (GYE) containing Czapek's salts. The exact composition of the medium is given in Table I.

TABLE I

Composition of the Medium Used to Prepare the Assay Plates

| Component | Grams/Liter |
| --- | --- |
| Glucose | 5.0 |
| Yeast Extract | 1.0 |
| Agar | 15.0 |
| MgSO$_4$ | 0.5 |
| FeSO$_4$ | 0.01 |
| NaNO$_3$ | 6.0 |
| KCl | 0.50 |

Obtusastyrene was incorporated into the culture medium at five concentrations by dilution of an acetone stock solution containing 0.01 gram solute/ml. The solute concentration of each acetone dilution was such that 10 ml of each dilution when added to 200 ml of the culture medium (distilled water containing the inorganic salts) provided a final solution concentration in the culture media of 2, 4, 8, 16 and 31, respectively. The acetone solution and the salt solution were mixed in a high-speed blender for 2 minutes to reduce the size of the precipitated particles of obtusastyrene and to disperse the compound uniformly in the medium. Most of the acetone was purged from the mixtures by intermittent, gentle heating for 10 minutes and by letting them stand for several hours afterward. To determine whether residual acetone in the medium affected fungal growth, an acetone control was prepared in addition to the control composed of nutrient medium only.

At this state of preparation, the media containing the various concentrations of obtusastyrene and of the controls were at pH 4.2 to 4.3. The media for each concentration were completed by the addition of glucose, Difco yeast extract, and agar before sterilization in an autoclave for 20 minutes at 15 psi. During sterilization the media containing the obtusastyrene turned reddish yellow while the controls remained colorless. Cooled media were poured into sterile Petri dishes, and each dish was inoculated in the center with a small uniformly-sized agar block cut from a five-day-old culture of Pestalotia or Chaetomium. The inoculated plates, prepared in triplicate for each concentration, were incubated at 23° C.

The fungal colony on each plate formed a nearly circular disk growing outward from the center. The minimum distance across each colony was the criterion of growth and was measured daily beginning 2 days after inoculation and continuing until the control colonies had reached the rims of the plates. For the fast-growing Pestalotia this limit was reached nine days after inoculation; for the slow-growing Chaetomium, measurements were continued until the thirteenth day after inoculation. After growth measurements were discontinued, plates were kept under observation to determine the reproductive activity of the fungi.

All final pH measurements were made 25 days after inoculation of the plates. At this time the average pH of all the Pestalotia plates was about 7.2. The average pH of the Chaetomium plates at the lower concentrations of obtusastyrene was 6.1; that for the higher concentrations was 7.6. Since Chatetomium grows best in acid media, the increase in pH contributed to a decrease in growth rate with time. Also, the slow growth of Chaetomium allowed time for the accumulation of the usual growth-inhibiting factors associated with fungus cultures in the Laboratory, i.e., drying of the agar, formation of metabolic by-products, and relative reduction of living space. These factors were not apparent, and did not significantly affect, the more rapidly growing Pestalotia cultures. The experiment had a minor inconsistency with regard to the growth of Chaetomium on the media containing the two lowest solute concentrations. A nonhomogenous dispersion of the compound throughout the media may have contributed to this inconsistency.

Figure 3:
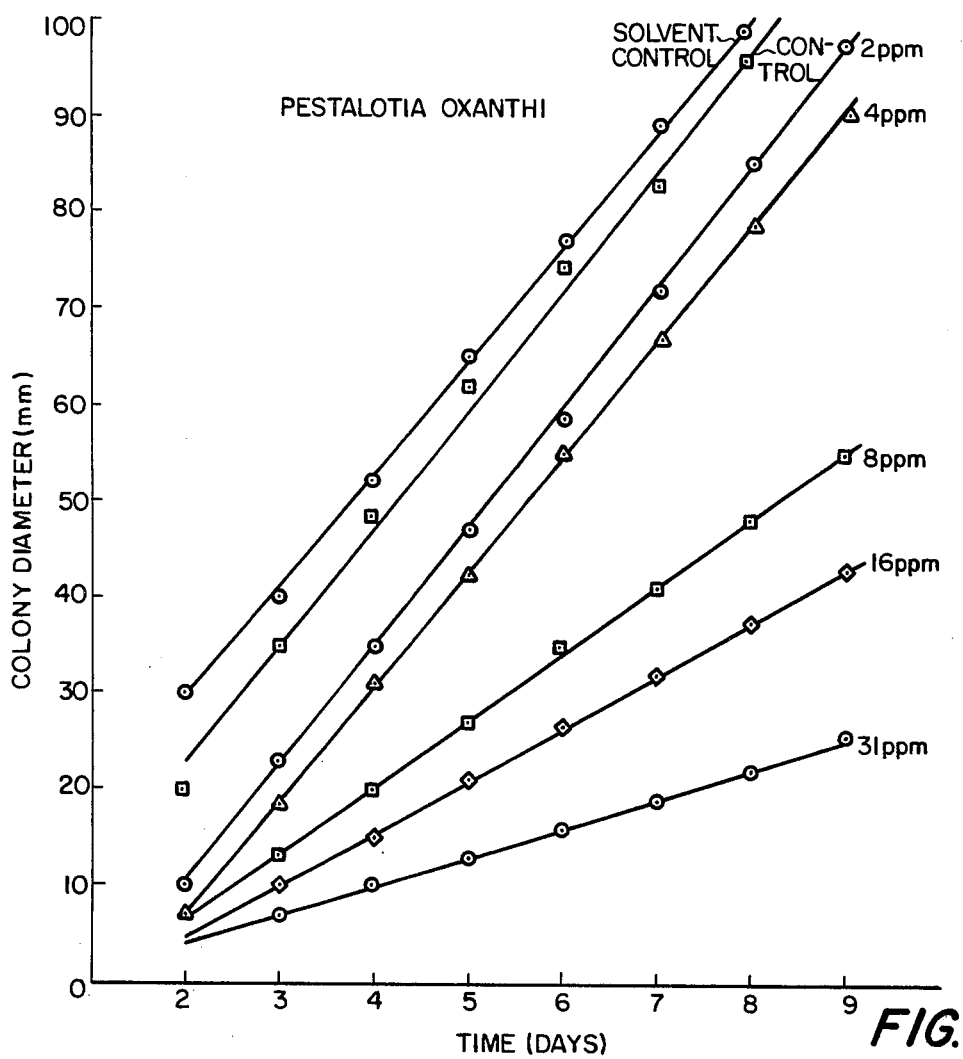
FIG. 3 shows the average colony diameter (minimum distance across each colony) as a function of colony age for *Pestalotia oxanthi*.
Figure 4:
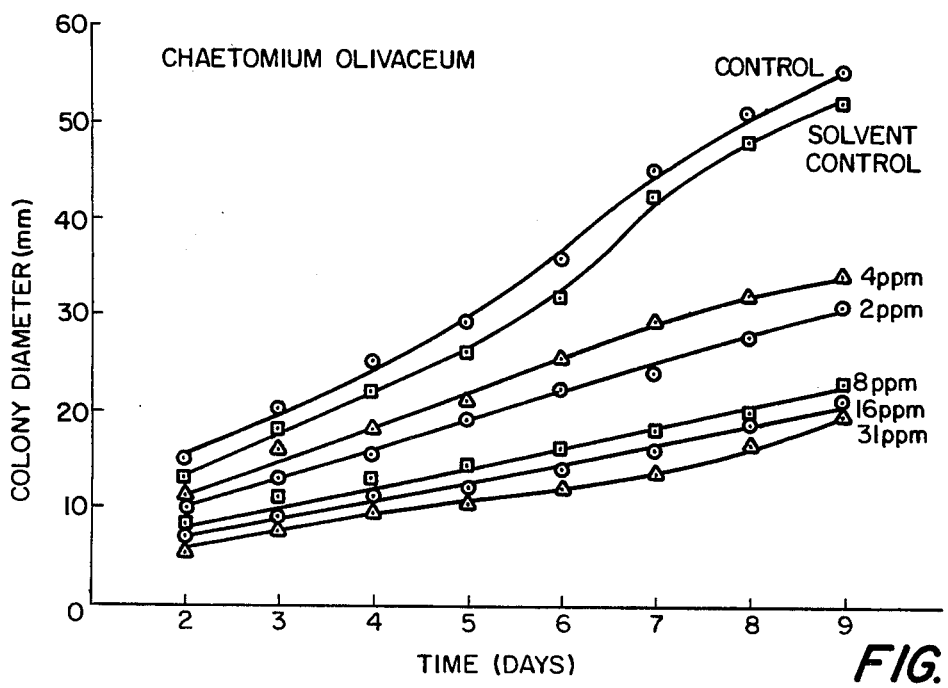
FIG. 4 shows the average colony diameter (minimum across each colony) as a function of colony age for *Chaetomium olivaceum*.

The test results are given in FIGS. 1 through 4. The average growth rate for each concentration of obtusastyrene is presented graphically for Pestalotia in FIG. 1 and for Chaetomium in FIG. 2. The day-by-day colony diameter (averaged from replicates) for each concentration of obtusastyrene is presented graphically for Pestalotia in FIG. 3 and for Chaetomium in FIG. 4. In FIGS. 3 and 4 the control and solvent control curves are quite similar, the differences being within the limits of experimental error. This fact indicates that trace amounts of residual acetone in the media did not significantly affect the growth of either of the two organisms.

In summary, obtusastyrene had an inhibitory effect upon the vegetative growth of both fungi, even at the lowest concentrations. Generally the growth rate was reduced as the concentration of obtusastyrene in the medium increased until a threshold value of about 8 ppm was reached for Pestalotia; beyond this an increase in toxicant concentration did not significantly increase inhibition throughout the duration of the experiment. A similar threshold concentration of about 8 ppm obtusastyrene was present for Chaetomium. At the highest concentration, obtusastyrene in the culture had a retarding effect on the reproduction of the tested fungi. Within nine days after inoculation, Pestalotia was producing masses of black pycnidia and conidia on all plates except those containing 16 and 31 ppm obtusastyrene. At these higher concentrations, pycnidia and conidia appeared only on the tiny agar cubes which were used for inoculating the plates. Even at the end of 25 days, no reproductive structures were produced except on the cubes. In those cultures of Chaetomium containing obtusastyrene at concentrations of 2 and 4 ppm, perithecia were present after 15 days. At concentrations of 8, 16 and 31 ppm, perithecia appeared on the inoculating cubes only, and in much smaller numbers than on cubes in the other cultures of this organism. At the end of 25 days, there were still no perithecia on the medium beyond the inoculating cubes. Possibly enough of the inhibitor diffused into the inoculating cubes to affect perithecium production.

The persistence of obtusastyrene in soft southern yellow pine was tested by a number of techniques. First, 2" pine discs impregnated with obtusastyrene were placed in a vacuum oven at 50° C. and at a vacuum of less than 5 mm Hg for 8 hours without any measureable loss of the compound. In the second test, discs similar to those above were subjected to a stream of sea water flowing at a rate of 2 cu. ft./min for seven months without any noticeable loss. The third test determined that the solubility of obtusastyrene in artificial water to be less than 10 ppm.

As the test results show, obtusastyrene has a powerful inhibitory effect upon the growth rate and reproduction on certain marine fungi and has great persistence in wood. These characteristics coupled with the probable sequential relationship between marine fungi and marine borers make the fungicide of this invention an excellent alternative to creosote in a marine environment.

Obviously many modifications and variations of the present invention are possible in light of the above teachings. It is therefore to be understood that within the scope of the appended claims the invention may be practiced otherwise than as specifically described.

What is claimed and desired to be secured by letters patent of the United States is:

1. A method of rendering wood resistant to marine fungical growth which comprises impregnating said wood with obtusastyrene.

2. A method of treating wood for eradicating marine fungical growth thereon which comprises contacting said wood with obtusastyrene.

3. The method of claim 2 wherein obtusastyrene is dissolved in a solvent.

4. The method of claim 3 wherein said solvent is selected from the class consisting of acetone, ethanol and benzene.

* * * * *